US006734449B2

(12) United States Patent
Peter et al.

(10) Patent No.: US 6,734,449 B2
(45) Date of Patent: May 11, 2004

(54) DEVICE FOR DETECTING THE LOCATION OF AN EDGE OF A TRANSPARENT MATERIAL, WEB EDGE CONTROL AND PRINTING PRESS

(75) Inventors: Karlheinz Walter Peter, Molfsee (DE); Rolf Johannes Spilz, Gettorf (DE); Patrick Metzler, St. Wendel (DE); Stefan Theden, Kiel (DE)

(73) Assignee: NexPress Solutions LLC, Rochester, NY (US)

( * ) Notice: Subject to any disclaimer, the term of this patent is extended or adjusted under 35 U.S.C. 154(b) by 301 days.

(21) Appl. No.: 09/990,047

(22) Filed: Nov. 20, 2001

(65) Prior Publication Data

US 2003/0094587 A1 May 22, 2003

(51) Int. Cl.[7] .......... G01N 21/86

(52) U.S. Cl. .......... 250/559.36; 250/559.09; 250/225; 356/614

(58) Field of Search .......... 250/225, 559.09, 250/559.36, 223 R, 559.45, 559.46, 559.48; 356/614, 364, 368, 429

(56) References Cited

U.S. PATENT DOCUMENTS

| | | | | |
|---|---|---|---|---|
| 5,107,131 A | * | 4/1992 | Okada et al. | 250/559.09 |
| 5,666,199 A | * | 9/1997 | Hess et al. | 356/364 |
| 6,175,419 B1 | * | 1/2001 | Haque et al. | 356/429 |
| 6,201,603 B1 | * | 3/2001 | Miura | 356/615 |
| 6,521,905 B1 | * | 2/2003 | Luxem et al. | 250/559.09 |

FOREIGN PATENT DOCUMENTS

| | | |
|---|---|---|
| GB | 627228 | 8/1949 |
| GB | 956636 | 4/1964 |

OTHER PUBLICATIONS

Schneider, Henning: Seitenkantenregelung laufender Warenbahnen. In: Siemens–Zeitschrift 46, 1972, H. 5, pp. 349–352.

JP 1–202604 A., In: Patents Abstracts of Japan, P–958, Nov. 13, 1989, vol. 13, No. 502.

* cited by examiner

*Primary Examiner*—Patrick J. Lee
(74) *Attorney, Agent, or Firm*—Lawrence P. Kessler

(57) ABSTRACT

The invention relates to a device for detecting the location of an edge (2) of a transparent, anisotropic material (3,3') comprising at least one sensor (1) with a light source (4), two polarization filters (6,7) with transmission axes (8,9) meeting at a 90° angle as well as a light detector (10), whereby the light source (4) and one polarization filter (6) are located on one side of the edge (2) to be detected and the second polarization filter (7) and the light detector are located on the other side.

This type of device is to be configured in such a way that it can be used for detecting material (3,3') with optical axes (14) in various directions without requiring assembly. This is achieved by at least one of the sensors (1) being configured and/or adjustable so that various angles (32) between the transmission axis of the first polarization filter (6) and the optical axis (14) of the transparent, anisotropic material (3,3') are possible. In addition, the invention is equipped for a web control edge (16) and printing press with such a web edge control.

14 Claims, 4 Drawing Sheets

16 12 11" 4 1 0° 12" 3,3' 12' 6 11 5 11' 2 19 13 7 17 17 18 10 30 20 20 15

10
24
23
5
Z
X
9
Y
7
-45°
22
22
2
5
32
5
22
E
3
45°
14
0°
25
25
1
8
Z
Y
X
+45°
6
21
21
19
12
4

DEVICE FOR DETECTING THE LOCATION OF AN EDGE OF A TRANSPARENT MATERIAL, WEB EDGE CONTROL AND PRINTING PRESS

FIELD OF THE INVENTION

The invention relates to a device for detecting the location of an edge of a transparent, anisotropic material, comprising at least one sensor with a light source, two polarization filters with transmission axes meeting at a 90° angle as well as a light detector, whereby the light source and one of the polarization filters are located on the edge to be detected and the second polarization filter and the light detector are located on the other side.

The invention further relates to a web edge control with such a device, a control device and a web edge adjustment device as well as a printing press with such a web edge control.

BACKGROUND OF THE INVENTION

A device for detecting the location of the edge of a transparent material is known from U.S. Pat. No. 5,751,443, whereby such light is to be directed on the transparent material so that it is reflected and then the reflected light is detected, in order to determine the location of an edge. The problem with a sensor using this method is that, if the material is soiled, the reflection properties are weakened, and thus the detection of the location of the edge is inaccurate or impossible. This is particularly true of continuous webs that transport goods, as well as printing presses, particularly electrophotographic printing presses that are equipped with a transparent web to convey printing substrates. Such web edges must, however, be detected, in order to adjust the location of the web.

A device from DE 199 06 154.8 of the type mentioned at the beginning was suggested to solve this problem. Its operating principle is based on the fact that polarization filters with transmission axes meeting at a 90° angle allow no penetration of light, since such polarized light passes only through the first polarization filter, which is blocked by the second polarization filter. If an anisotropic material with an excellent optical axis is introduced between the polarization filters, a beam or partial bean may occur, whose polarization direction is turned to 90°. This light penetrates the second polarization filter, so that a clear image of the material edge is produced on the light detector. This image is basically much more resistant to soiling than the image based on a reflection. However, the problem with this suggestion is that a beam or partial beam with a turned polarization direction does not occur if the light along the optical axis of the transparent material enters into this material. The light must then form an angle to the optical axis, which ensures that there is an easily detectable amount of light that is turned in its polarization direction. However, due to the manufacturing procedure and stress, the optical axis of transparent, anisotropic materials also has different alignments with a material of the same chemical composition. Such a device must thus be aligned with the respective optical axis in which the beam is turned in its polarization direction with an easily detectable intensity. Due to the above-mentioned reasons, this alignment must, however, be repeated with each piece of material to be detected. Where a wet to convey a product is concerned, each change of the web to a new web requires an alignment of the sensor with the optical axis of the new web. This problem may also well occur with an increase or decrease of the stress of the web.

SUMMARY OF THE INVENTION

In contrast to this suggestion, the task of the invention is to configure a device for detecting the location of an edge of a transparent, anisotropic material that does not require assembly for the detection of material with optical axes in various directions.

This task can be achieved by having at least one sensor of this type that can be arranged and/or is configured, so that various angles between the transmission axis of the first polarization filter and the optical axis of the transparent, anisotropic material are possible.

Thus a device would be provided that can detect the edge of a transparent, anisotropic material and whereby, by means of a simple tilting motion or another change of position with change in the angle direction of the polarized light, a position can be achieved in which the alignment to the optical axis of the respective material required to detect the material is possible. In this manner, it is possible to obtain the exact location of this type of material edge, which is relatively resistant to soiling and which thus solves the problem stated at the beginning, particularly where continuous web edge controls and webs transporting material, such as the web edge control for transparent, anisotropic webs of electrographic printing presses, are concerned.

The problem of the different optical axes occurs primarily because the optical axes of webs have various directions as a result of the manufacturing process and that the detection and adjustment of the location of such a web is difficult. The device according to the invention provides a web edge control in which the optical path is directed or can be directed to the edge of a transparent, anisotropic web to be detected in such a way that all possible courses of optical axes as a result of the change of the optical axes of the/a web can be adjusted, without requiring assembly. To this end, a sensor can be arranged such that it can be tilted, and several sensors can be arranged at various angle positions and the corresponding sensor can be selected or the optical path of one sensor of this type can be configured so that it is adjustable, and thus it and the polarized light can take various angle positions to the material to be detected and thus to its optical axis.

Particularly in the case of printing presses, the device according to the invention can reduce the maintenance costs, the use of assembly staff, and the machine downtime during a change of the web. Also with a change in the stress of a web and a concordant change of the location of the optical axis, the device can be aligned with the direction of the optical path without great expense. Another use for the invention is the detection of the edge of individual piece of material, since in this case as well, the different course of the optical axes must be taken into account.

The device according to the invention provides a simple means such that the polarized light takes an angle position to the material, in which a turn of the light emitted from the first polarization filter passes through the material to be detected to a sufficient degree to detect an edge, whereby an angle between the transmission axis of the first polarization filter and the optical axis of the transparent, anisotropic material is preferably selected, in which the best possible image of the edge on the light detector can be achieved. An optimum is achieved with a 45° angle, although an angle within the range of 25° and 65° will suffice to show an image of an edge.

There are various ways to configure the placement of the sensor in various positions to achieve the above-mentioned angle or another alignment of various angle positions of the polarized light to the material to be detected. It can be set up so that the angle between the transmission axis and the optical axis is exactly positioned or so that an angle position of a sensor is selected that lies in the 25° to 65° angle range. It is often sufficient to use two defined angle positions and that the angle position to the respective material is selected in which the edge is better shown. However, a plurality of multiple defined angle positions can also be envisaged, whereby the angle position to the respective material is selected in which the edge is better shown. The latter or an exact positioning of the angle is useful if the directions of the optical axes of the material to be detected is not limited to a particular angle range, but the optical axes can take all the various directions possible or, if a good image of the edge requires that the most optimal angle be selected, that the best optimal angle is selected, such as when a material of reduced transparency, caused by soiling, for example, is to be detected.

The sensor may also be tilted manually into the various positions and locked in this position. This can be implemented with any simple mechanics. A drive may also be used, which places a sensor in the most optimal position of possible positions with various angle positions. This is an advantage if the sensor is mounted on a part of the machine that is difficult to reach. In addition, a control can be used that is connected with the light detector and that the angle position for the image of the edge is selected on the light detector. This can, for example, permit the placing of a sensor in its optimal position. For example, the control can ensure that several positions are switched through and that the most contrasting image of the edge is selected. But it can also select the most optimal optical path from angle positions of several optical paths installed in any manner, or adjust an optical path in a corresponding manner. This type of device is very comfortable, since no further operating effort is required. If the material to be detected concerns individually transporter pieces that have optical axes in various directions, then this type of control is a very useful solution, since it automatically ensures very good detection of the edges.

In addition, a control can be further configured so that it adjusts the intensity of the light source and/or the responsivity of the light detector. The advantage of this control is that the device reacts automatically to a change of conditions and thus ensures a flawless image of the edge. Such changes may be due to some contamination, or because materials of various intensities of transparency are to be detected.

The control can adjust the set points on the basis of a corresponding algorithm of a program, or it is possible that the control has programmed set points for defined positions. In this manner, an optimal positioning is ensured.

The light detector may comprise several optical receiving components: for example, it may be configured as rows of optical receiving components, e.g., forming a CCD row, or it is possible that the light detector is configured as a flat receiver. With such arrangements, digital set points for further processing in an electronic control have been produced. In this sense, a flat receiver has the advantage that, by means of a single receiver, the inclined position of an edge can be detected.

BRIEF DESCRIPTION OF THE DRAWINGS

In the detailed description of the preferred embodiment of the invention presented below, reference is made to the accompanying drawings, in which.

DETAILED DESCRIPTION OF THE INVENTION

Figure 1:
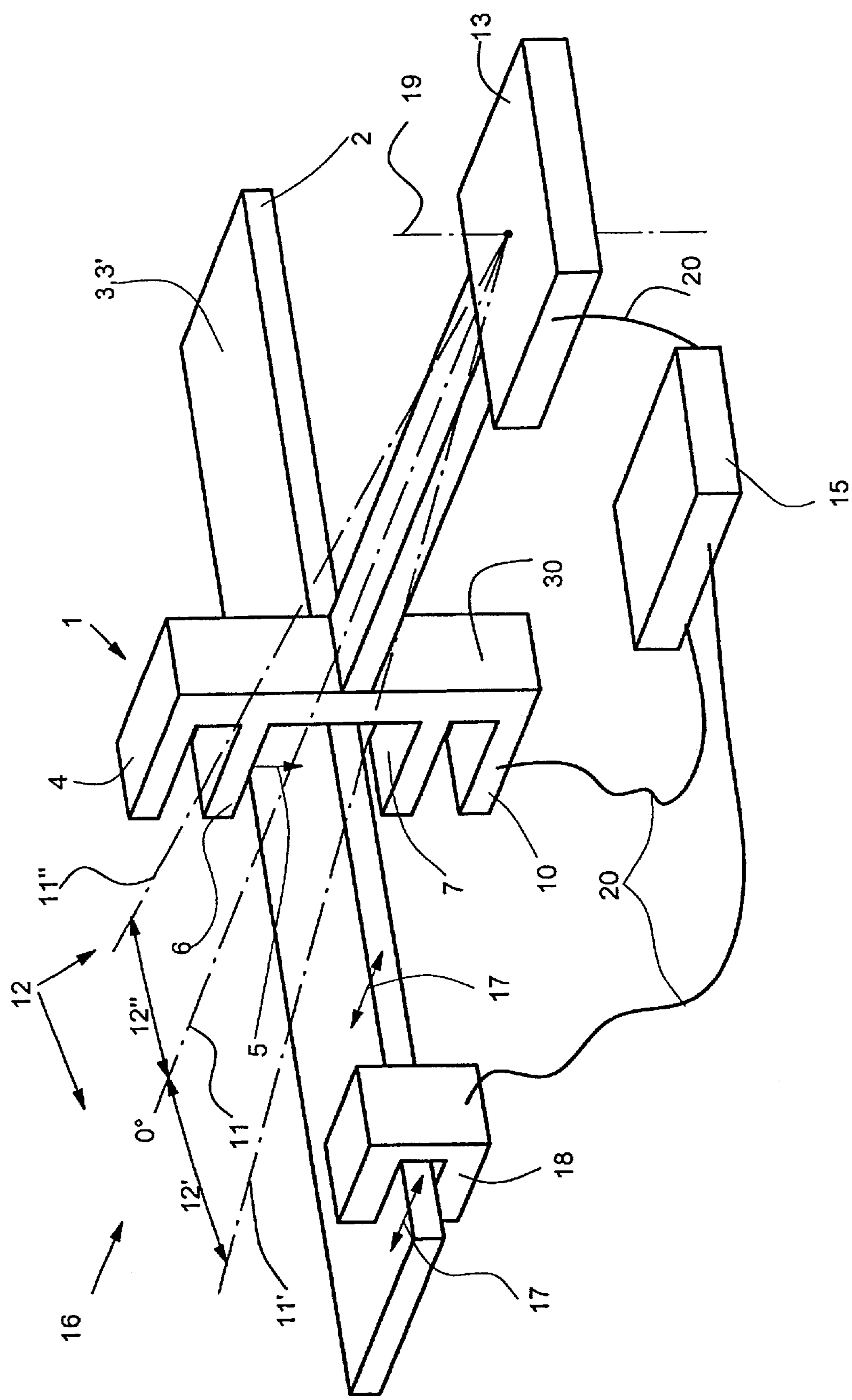
FIG. 1 an exemplary embodiment of a web edge control according to the invention with a device according to the invention, which is configured as a swiveling sensor FIG. 2 the operating principle of such a sensor FIGS. 3*a*, 3*b* and 3*c* The effects of various angle positions of the polarized light on a material with various angle positions of the optical axis with respect to the degree of effectiveness of a sensor and FIG. 4 an example for various angle positions of the optical axis of a web caused by the manufacturing process.

FIG. 1 illustrates an exemplary embodiment of a web edge control 16 according to the invention with a device according to the invention that is configured as a swiveling sensor 1. The sensor 1 is used to detect an edge 2 of a transparent anisotropic material 3, for example, a transparent web 3'.

The sensor 1 consists of a light source 4 and two polarization filters 6, 7, whose transmission axes 8, 9 meet at a 90° angle. In addition, a light detector 10 is arranged that may be configured as a CCD row, for example, or as an array of receiving components. The light source 4 and the first polarization filter 6 are located on one side with respect to the edge 2 of the transparent, anisotropic material 3 or 3' to be detected, and the second polarization filter 7 with the light detector 10 is located on the other side of the material 3, 3'.

The invention recommends that the light source 4, the polarization filters 6,7 as well as the light detector 10 be configured in such a manner that the sensor 1 can take various positions 11, 11', 11", . . . in which the polarized light 5 can take various angle positions 12, 12', 12", . . . to the material 3, 3' to be detected, in order to find an angle 32 of the transmission axis 8 of the first polarization filter 5 at the optical angle 14 of the material 3, 3' (see FIG. 2), in which an accurate detection of the edge 2 is possible. To this end, the sensor 1 is configured in such a way that the light source 4, the polarization filters 6, 7 as well as the light detector 10 are located on a common carrier 30, which can be swiveled around a swivel axis 19. This swiveling capacity is configured in such a way that the sensor 1 can be moved from the position 11 indicated into other positions 11', 11", . . . in order to select a position 11, 11', 11", . . . in which the polarized light 5 with its optical axis 14 of the material 3, 3' forms an angle that is wide enough to ensure a portion of the light, whose polarization direction 22 is turned is taken, and which is sufficiently intensive that it can be detected with the light detector 10. To this end, the sensor 1 and thus the polarized light 5 can take the angle positions 12' or 12" illustrated in the exemplary embodiment. As a result, it is possible to envisage both of the illustrated positions 12', 12", or any of the angle positions 12 within the mechanically possible swiveling range can be envisaged as possible positions.

This type of sensor 1 may be configured in such a way that it may be manually swiveled and locked in various positions 11, 11', 11", . . . . In the exemplary embodiment illustrated, a drive 13 is used that can place the sensor 1 in the various positions 11, 11', 11", . . . . For this purpose, a control 15, which is connected by a connecting line 20 to the light detector 10 and which selects a position 11, 11', 11", of sensor 1 and which can take a position 11, 11', 11", . . . in which the edge 2 is clearly shown on the light detector 10. If such a clear image is achieved, then the control 15 allows a positioning movement 17, based on the values, determined by the light detector 10, to obtain the targeted position of the edge 2 by means of a web edge control device 18, which is likewise connected to the control 15 by means of a connecting line. The drive 13, the control 15 and the web edge control device 18 constitute a principal drawing. This component may be any configuration, whereby such a drive as well as the control can also be positioned in the above-mentioned vertical axis.

Figure 2:
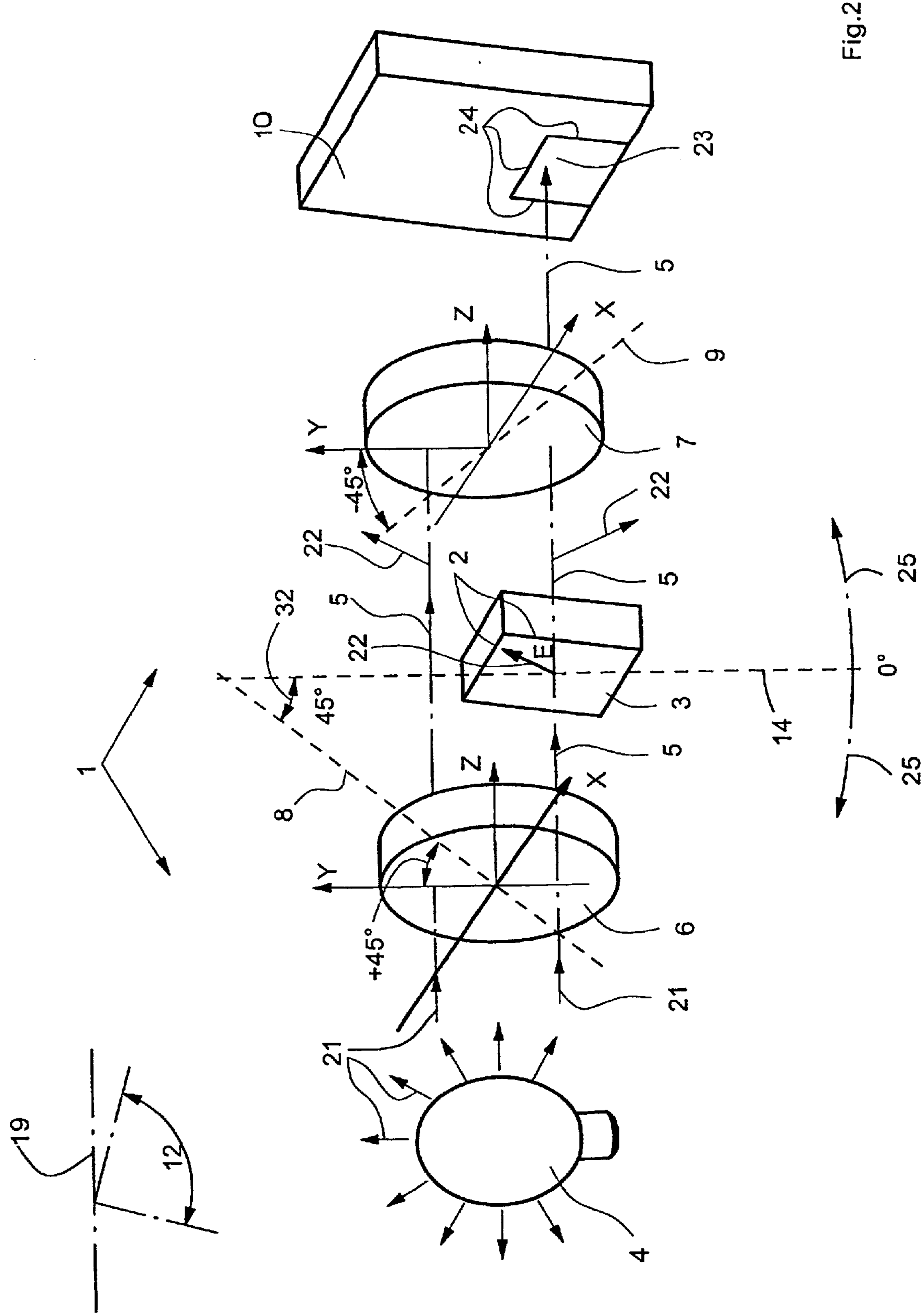

FIG. 2 shows the operating principle of the sensor 1. The light source 4 emits unpolarized light 21, whereby the only polarized light 5 passes through the first polarization filter 6 that has a polarization direction 22 lying in its transmission axis 8. In the illustrated example, the transmission axis 8 is located on a coordinate system x, y, z at an angle of +45° on the y-axis in the y-z plane. As long as this polarized light 5 is not hitting a transparent, anisotropic material 3 or 3', the polarization direction 22 is maintained and hits the second polarization filter 7, whose transmission axis 9 is turned so that it lies at a 90° angle to the transmission axis 8 of the first polarization filter 6, thus forming a 45° angle to the y axis appearing in the y-z plane. This prevents the polarized light 5 of the rays passing over the top half of the transparent material 3 from penetrating the second polarization filter 7. The rays of the polarized light 5 act differently, in that they hit the transparent, anisotropic material 3. With respect to a portion of the light 5, during the course of the optical axis 14 of the material 3, the polarization direction 22 is turned, which causes this portion of the light 5 to be polarized in the direction of the transmission axis 9 of the second polarization filter 7, thus permitting this portion of light 5 to penetrate the second polarization filter 7. The polarized light 5 penetrating the polarization filter 9 is detected by a light detector 10. An illuminated surface 23 is thus produced by this polarized light 5. As a result, the edges 2 of the material 3 are also shown as edges 24. Thus the location of the transparent material 3 and its edge 2 are accurately detected. The remaining surface of the light detector stays dark, since the turned polarized light 5 that did not penetrate the transparent material 3 in its polarization direction 22 is blocked by the second polarization filter 7.

The invention uses the setup of the transmission axis 8 of the first polarization filter 6 at the optical axis 14 to ensure, by means of the selected angle position 12, that the polarized light 5 approaching the light detector 10 has the proper intensity to be able; to detect the edges 2 as clearly shown by edges 24. The swiveling of the angle position 12 makes it possible to obtain the dash and dot axis 19 in the direction of the dash and dot arrow indicating the angle positions 12, as illustrated in FIG. 1. Since the swiveling occurs in the y-z plane, the angle position 12 changes between the polarized light 5 and the material 3, 3' to be detected, and thus between the transmission axis 3 and optical axis 14. If the change of the angle position 25 of the optical axis 14 of the material 3, 3' likewise occurs in the y-z plane, as illustrated by the dash and dot arrow, symbolizing the angle position 25, then within this plane, a coordination of the course of the transmission axis 8 to the optical axis 14 can be obtained, which ensures that the turning of the polarization direction 22 is sufficient.

Figure 3C:
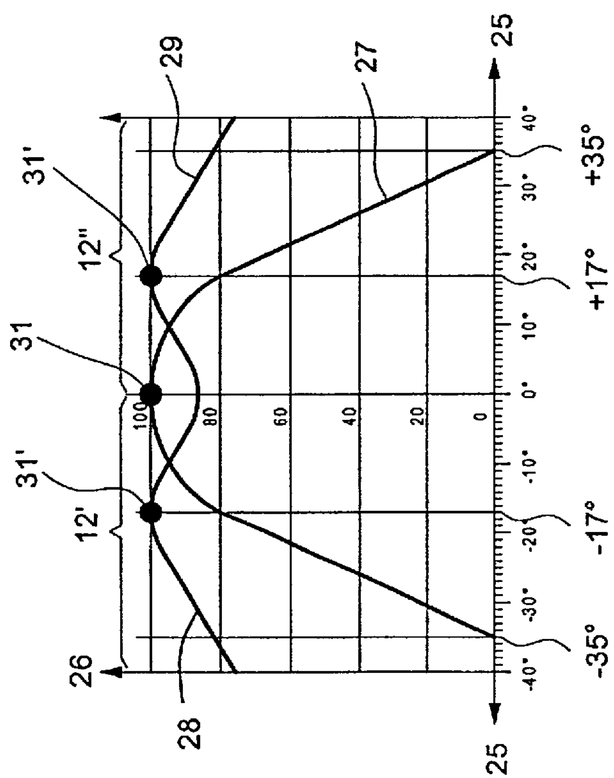
Figure 3B:
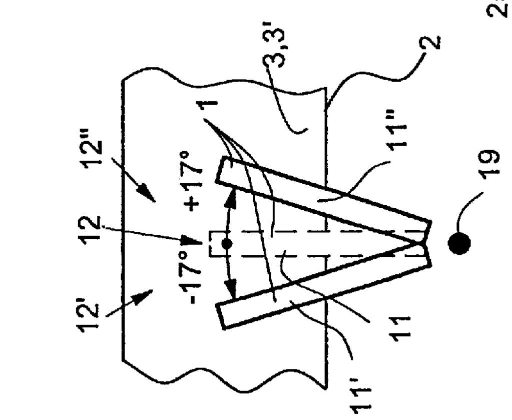
Figure 3A:
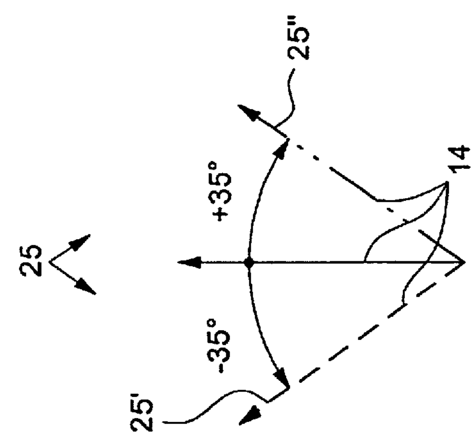

FIGS. 3*a*, 3*b* and 3*c* show the effects of different angle positions 12, 12', 12", of the polarized light 5 to a material 3, 3' with various angle positions 25, 25', 25", . . . of the optical axis 14 with respect to the degree of effectiveness 26 of a sensor 1.

In addition, FIG. 3*a* shows the various angle positions 25 of the optical axis 14 of the material 3, whereby the angle position 25' is located at −35° and the angle position 25" is located at +35° The area in between is the customary swiveling space of angle positions 25 of optical axis 14 during the manufacturing of the transparent web 3".

FIG. 3*b* shows swiveling motions of the sensor 1 that are set up so that the sensor 1 can detect the edge 2 of a material 3, 3', although different angle positions 25 of the optical axis 14 of the transparent materials 3, 3' appear. The exemplary embodiment of FIG. 3*b* recommends in this case that the sensor 1 take an angle position 12' of −17° or an angle position 12" of +17°. It is thus not located in the dot and dash area of the 0° position 11, but in one of the position 11' or 11" facing the material 3 or 3' to be detected. Thus the swiveling of the sensor 1 is only an example that the polarized light 5 can take various angle positions 12, 12', 12", . . . to the material 3, 3' to be detected. Further possibilities, such as placing the polarized light 5 in various angle positions 12, 12', 12", . . . are conceivable.

FIG. 3 shows the effect of the angle positions 12 or 12' on the degree of effectiveness 26 of the sensor 1. Here, the curve 27 is shown in comparison with the degree of effectiveness 26 of the sensor 1, which is located in the dot and dash area of position 11 in FIG. 3*b*. Here the polarized light 5 in the point 31 takes an angle position of 0° to the material 3, whereby, by means of the relocation of the transmission axis 8 at 45° to the optical axis 14 (see FIG. 2), the maximum possible effectiveness 26 of 100% is achieved. This type of positioning has the disadvantage, however, that the effectiveness up to the angle 25 of the optical axis 14 drops from −35° or +35° to 0 and sensor 1 cannot function.

The exemplary embodiment thus recommends that it must be possible to place the sensor 1 in the second position 11' and 11", as illustrated in FIG. 3*b*. The effect is plotted by means of the curves 28 and 29 in FIG. 3*c*. Here the curve 28 shows the effectiveness of a sensor 1, wherein the polarized light 5 is located in the angle position 12', thus at −17° with respect to the perpendicular line on the surface of the material 3. By contrast, the other curved portion 29 extends to the curved portion 28 in the positive area and represents the effectiveness 29 of a sensor 1, wherein the polarized light 5 in the angle position 12" is located at +17° with respect to the perpendicular line on the surface of the material 3. Here both angle positions 12' and 12 'are laid out in such a way that the optimal effectiveness 26 in these angle positions and thus with 17° or +17 is ensured In these points 31 and 31', 100% of the possible effectiveness 26 can be achieved, so that in the angle positions 12' and 12" of the polarized light 5 respectively, the transmission axis 8 is located at an angle of 45° to the optical axis 14 (see FIG. 2). It can thus be seen how already, by taking two possible angle positions 12' and 12", it is possible for a transparent material 3, 3' to be detected whose optical axis 14 moves in an angle range 25 of way over +40° to −40', whereby with an angle of 35° of the effectiveness 26 always still lies at a minimum of 80°. Thus there are materials of ±45° with respect to the 0° position that can still be clearly detected up to the angle deviations 25 of the optical axis 14, which at the position 12 is not possible.

Figure 4:
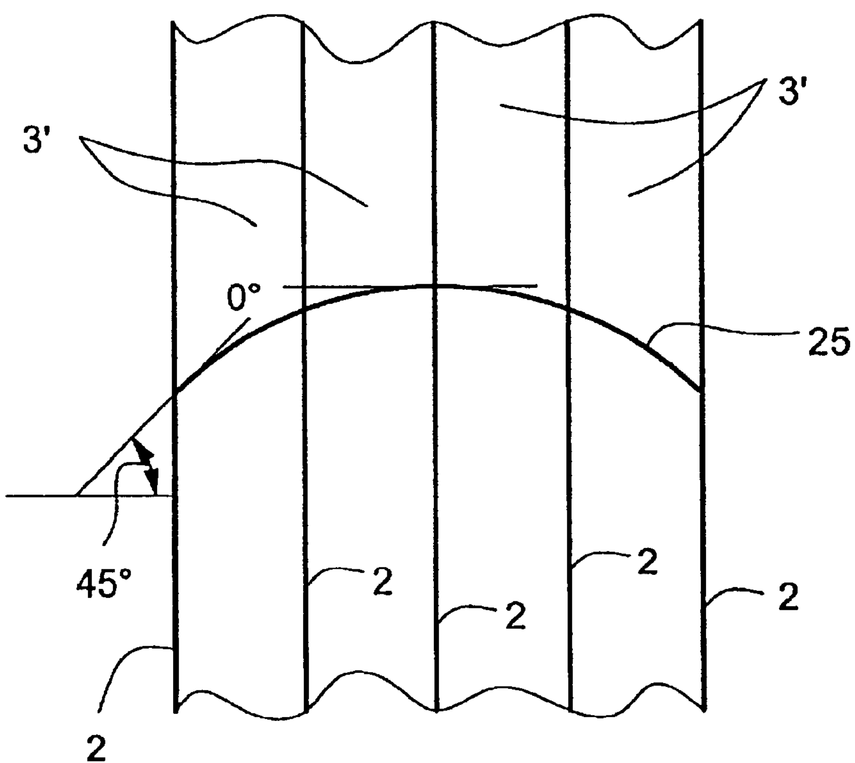

FIG. 4 shows an example for angle positions 25 of the optical axis 14 of transparent, anisotropic webs 3' resulting from the manufacturing process. When such webs 3' are produced, wide webs are often are manufactured for economic reasons, from which several 3' webs are then cut. Due to the manufacturing process, a course of angle positions 25 of the optical axis 14 occurs, which corresponds to the course plotted. Thus the course of the optical axis 14 may vary between 0° and a maximum of ±45, for example, whereby certain angle differences can be found across the entire width of the individual webs 3'. The sensor 1 must thus be adjusted to the angle position 25 of the optical axis 14 in the area of a web 3' in which the edge 2 is supposed to be detected. This can easily be done by means of swiveling the sensor 1 according to the invention or by means of another change of the angle position 25, 25', 25", . . . of the polarized light 5, and it is possible to accurately detect such webs 3 and adjust the position of the webs 3' by a positioning movement 17 based on this detection. This is of particular importance with the electro-photographic printing press, since in this case, webs 3' are used in the manner illustrated in FIG. 4 and that, with a change of a web 3', it must be possible to immediately align a web edge control 16 with the new course of the optical axis 14, in order to continue operating the press with minimum downtime. In addition, the invention makes it possible for the operator to change the web 3' himself, since the setting of sensor 1 takes no effort.

The illustrations are, of course, only examples; they show one way in which a sensor 1 and a web edge control 16 can be produced and explain the operating principle of the invention. Various positions of a sensor 1 can not only be achieved by swiveling motions around a swivel axis 19, best it is also possible to achieve an even larger positioning area with other mechanical devices for positioning the sensor 1 in various positions 11, 11', 11", . . . . In addition, it is also possible to use any position 11 of the sensor 1 or a defined number of several positions 11, 11', 11", . . . . The respective embodiment shows how such a sensor 1 can be concretely used.

Of course, instead of a mechanical positioning—as mentioned above—an arrangement of several sensors 1 can also be used, or the angle positions 12, 12', '12", . . . may be determined by means of a selection of a sensor 1 from positioned sensors 1 in various angle positions 12, 12', '12". It is also possible to use a sensor 1 with optical means with various angle positions 12, 12', '12', . . . from which one is selected to detect the edge 2 of a material 3, 3'. Adjustable optical means may also be envisaged.

The invention has been described in detail with particular reference to certain preferred embodiments thereof, but it will be understood that variations and modifications can be effected within the spirit and scope of the invention.

Parts List

- 1 Sensor
- 2 Edge
- 3 3,3' Transparent, anisotropic material
- 3' Transparent web
- 4 Light source
- 5 Polarized light
- 6 First polarization filter
- 7 Second polarization filter
- 8 Transmission axis of the first polarization filter
- 9 Transmission axis of the second polarization filter
- 10 Light detector
- 11' 11", . . . Position of the sensor
- 12' 12", . . . Angie positions of the polarized light to the transparent material, e.g., as angle positions of a sensor
- 13 Drive of the sensor
- 14 Optical axis of the transparent material/transparent web
- 15 Control
- 16 Web edge control
- 17 Positioning movements for the web edge
- 18 Web edge control device
- 19 Swivel axis
- 20 Connecting lines
- 21 Unpolarized light
- 22 Polarization direction
- 23 Illuminated surface of the light detector
- 24 Edges shown
- 25', 25" Angle positions of the optical axis of the transparent, anisotropic material
- 26 Degree of effectiveness of the sensor
- 27 Degree of effectiveness of a sensor with an angle position 25 of the optical axis 14 between −40° and +40°, if the angle position of the sensor at 0° produces the optimum (i.e., the transmission axis 8 forms an angle of 45° to the optical axis 14)
- 28 Degree of effectiveness of a sensor with an angle position 25 of the optical axis 14 between −40° and 0°, if the angle position of the sensor at −17° produces the optimum (i.e., the transmission axis 8 forms an angle of 45° to the optical axis 14)
- 29 Degree of effectiveness of a sensor with an angle position 25 of the optical axis 14 between 0° and +40°, if the angle position of the sensor at +17° produces the optimum (i.e., the transmission axis 8 forms an angle of 45° to the optical axis 14)
- 30 Common carrier
- 31,31' Points of the maximum effectiveness (100%) by means of a location of the transmission axis 8 with an angle of 45° to the optical axis 14
- 31 Point with one possible angle position
- 31' Points with two possible angle positions
- 32 Angle between the transmission axis 8 of the first polarization filter and the optical axis 14 of the transparent, anisotropic material

What is claimed is:

1. Device for detection of the location of an edge (2) of a transparent, anisotropic material (3,3') comprising: at least one sensor (1) with a light source (4), two polarization filters (6,7) with transmission axes (8,9) meeting at a 90° angle as well as a light detector (10), whereby the light source (4) and one polarization filter (6) are located on one side of the edge (2) to be detected and the second polarization filter (7) and the light detector (10) are located on the other side and whereby at least one of the sensors (1) can be arranged and/or configured so that various angles (32) between the transmission axis (8) of the first polarization filter (6) and the optical axis (14) of the transparent, anisotropic material (3,3') are possible.

2. Device according to claim 1, characterized in that an angle (32) is selected in which a turn of the light (5) emitted from the first polarization filter (6) passes through the material (3,3') to be detected to a sufficient extent that it can detect an edge (2).

3. Device according to claim 2, characterized in that an angle (32) is selected in which one of the best possible images of the edge (2) on the light detector (10) is possible.

4. Device according to claim 3, characterized in that the transmission axis (8) of the first polarization filter (6) to the optical axis (14) of the transparent material (3,3') forms an angle in the 25° to 65' range.

5. Device according to claim 1 characterized in that taco defined angle positions (12', 12") have been used and the angle position (12', 12") in which the edge (2) is better shown is selected for the respective material (3, 3').

6. Device according to claim 5 characterized in that that a drive (13) is used that places the one sensor (1) in the optimal position (11, 11', 11", . . . ).

7. Device according to claim 2 characterized in that a control (15) is used that is connected to the light detector (10) and that the angle position (12', 12") for showing the edge (2) is selected on the light detector (10).

8. Device according to claim 7, characterized in that a control (15) is used that adjusts the intensity of the light source (4).

9. Device according to claim 8, characterized in that a control (15) is used that adjusts the responsivity of the light detector.

10. Device according to claim 9, characterized in that the control (15) has been programmed with set points for defined angle positions (12', 12").

11. Device according to claim 1 ,characterized in that the light detector (10) As constructed of several receiving components.

12. Device according to claim 1 characterized in that the light detector (10) is configured as a flat receiver.

13. Device according to claim 1 characterized in that the light detector (10) comprises a row of receiving components.

14. Web edge control (16) with a device according to claim 1 a control (15) and a web edge control (18), characterized in that at least one of the sensors (1) faces 'e edge (2) of a transparent, anisotropic web (3') to be detected is configured or arranged so that all possible courses of the optical axes (14) due to a change of the optical axis (14) of the/a web (3') can be taken.

* * * * *